United States Patent
Kramer (10) Patent No.: US 8,417,541 B1
(45) Date of Patent: Apr. 9, 2013

(54) MULTI-STAGE MODEL FOR PREDICTING PROBABILITIES OF MORTALITY IN ADULT CRITICALLY ILL PATIENTS

(75) Inventor: Andrew A. Kramer, Leesburg, VA (US)

(73) Assignee: Cerner Innovation, Inc., Lenexa, KS (US)

(*) Notice: Subject to any disclaimer, the term of this patent is extended or adjusted under 35 U.S.C. 154(b) by 869 days.

(21) Appl. No.: 12/549,153

(22) Filed: Aug. 27, 2009

(51) Int. Cl.
- *G06Q 10/00* (2006.01)
- *G06Q 50/00* (2006.01)
- *G06Q 40/00* (2006.01)

(52) U.S. Cl.
USPC .............................. 705/2; 705/3; 705/4

(58) Field of Classification Search .................. None
See application file for complete search history.

(56) References Cited

U.S. PATENT DOCUMENTS

| | | | |
|---|---|---|---|
| 6,294,339 B1 * | 9/2001 | Wunderink et al. | 435/6.11 |
| 6,533,724 B2 * | 3/2003 | McNair | 600/300 |
| 6,835,176 B2 * | 12/2004 | McNair | 600/300 |
| 7,395,216 B2 * | 7/2008 | Rosenfeld et al. | 705/2 |
| 7,433,827 B2 * | 10/2008 | Rosenfeld et al. | 705/2 |
| 7,713,211 B2 * | 5/2010 | Anderson et al. | 600/484 |
| 8,090,562 B2 * | 1/2012 | Snider et al. | 703/11 |
| 8,183,050 B2 * | 5/2012 | Shi et al. | 436/86 |
| 2009/0216556 A1 * | 8/2009 | Martin et al. | 705/3 |

FOREIGN PATENT DOCUMENTS

| | | | |
|---|---|---|---|
| EP | 1032908 A1 * | 9/2000 | |
| EP | 2153233 A1 * | 2/2010 | |

OTHER PUBLICATIONS

Schuster, Daniel "Predicting Outcome after ICU Admission" Chest 1992; 102:1861.70.*
Frick et al. "Medical futility: prediciting outcome of intensive care unit patients by nurses and doctors—A prospective comparitive study" Crit Care Med 2003 vol. 31, No. 2.*
El-Solh et al., "A comparison of severity of illness scoring systems for critically ill obstetric patients" Chest /110/5/ Nov. 1996.*

* cited by examiner

*Primary Examiner* — Robert Morgan
*Assistant Examiner* — Eliza Lam
(74) *Attorney, Agent, or Firm* — Shook, Hardy & Bacon LLP (57) ABSTRACT

Computerized methods in a clinical computing environment for predicting mortality in critically ill patients, that is, patients admitted to Intensive Care Units, are provided. In accordance with embodiments hereof, at least two distinctly different mortality prediction models (e.g., the Acute Physiology and Chronic Health Evaluation (APACHE®) model and the Mortality Probability Model at Admission ($MPM_0$) are utilized in a multi-stage fashion to determine, with better accuracy than may be provided by either mortality prediction model alone, the probability of mortality for critically ill adult patients.

13 Claims, 2 Drawing Sheets

FIG. 2.

MULTI-STAGE MODEL FOR PREDICTING PROBABILITIES OF MORTALITY IN ADULT CRITICALLY ILL PATIENTS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND

Models for measuring severity of illness and predicting hospital mortality for patients in Intensive Care Units (ICUs) have been around for quite some time. This has come about not only as a result of the desire to assess ICU performance by comparing observed and predicted mortality but also, at least in part, due to the more recent ability to capture data electronically.

Large data sets containing numerous measurements on a wide variety of patients has enabled the development of sophisticated predictive models of mortality. Without exception, these predictive models involve a one-step process. That is, information on a set of variables is collected and fed into a single logistic regression equation.

Two of the preeminent mortality prediction models for critically ill patients in the United States are the Acute Physiology and Chronic Health Evaluation (APACHE®) model and the Mortality Probability Model at Admission ($MPM_0$). Each of these mortality prediction models utilizes multiple variables in a single logistic regression equation to predict a patient's probability of mortality. However, there are substantial differences regarding what information is used in these models.

The APACHE® prediction methodology is based on the view that the core mission of intensive care is to treat disease and maintain physiological homeostasis. The central metric is the APACHE® score. It measures severity of illness during the first day after ICU admission, using the type and extent of acute physiological abnormality (the Acute Physiology Score or APS) and physiological reserve (age and co-morbid conditions). The APS is a sum of weights incurred by 17 physiologic parameters, the weights being determined by each physiologic measure's worst value within their first day in the ICU. It reflects a patient's response to treatment within the first ICU day. These components of the APACHE® score are used in the over 70 predictive equations that make up the APACHE® System. One such equation predicts mortality before hospital discharge. This equation contains 143 variables, including terms for the APS, age, seven comorbid conditions, the time between hospital admission and ICU admission, 116 diagnostic categories, the admission source, and five additional clinical variables. In summary, the APACHE® mortality prediction model collects information based primarily on physiologic parameters collected within the first day in the ICU, and supplemented by, among other things, specific information on diagnosis.

The $MPM_0$ mortality prediction model is a more simplistic model that utilizes information collected upon admission to the ICU or within one hour thereafter. It consists of 17 variables: 16 binary variables and the patient's age, as well as interaction terms between six of the binary variables and age. These variables were chosen to characterize a patient's acuity at the time of ICU admission, before being appreciably affected by ICU care. The $MPM_0$ model is a much smaller model than the APACHE® mortality prediction model, is based on information collected at or within the first hour post-admission, and expresses a patient's clinical condition upon admission.

While there is a correlation between the APACHE® and $MPM_0$ mortality model predictions ($R^2 \sim 0.4$), a fair proportion of the time they can give quite disparate predictions. For instance, in a sample of 4,072 admissions to twenty ICUs in a single calendar year, the two models yielded predictions that in absolute terms differed by more than 0.15 (15%) for 20% of the patients. Unequivocally, the variables and time frame for these two exemplary mortality prediction models are quite different and yet there is clearly pertinent information that is unique to each model.

SUMMARY

Embodiments of the present invention relate to methods in a clinical computing environment for predicting the probability of mortality before hospital discharge (hereafter referred to as "mortality") in critically ill adult patients, that is, adult patients admitted to Intensive Care Units. In accordance with embodiments hereof, at least two distinctly different types of mortality prediction models are utilized concurrently to determine, with better accuracy than may be provided by either mortality prediction model alone, the probability of mortality for critically ill patients.

In one embodiment, the present invention is directed to one or more computer-storage media having computer-executable instructions embodied thereon for performing a method in a clinical computing environment for predicting a probability of mortality for a patient admitted to an Intensive Care Unit. The method includes determining a length of a first Intensive-Care-Unit-day for the patient (e.g., under the APACHE® methodology); calculating a first mortality probability utilizing a first mortality prediction model (e.g., the APACHE® mortality prediction model), the first mortality prediction model being based on physiological data items collected within the patient's first Intensive-Care-Unit-day; calculating a second mortality probability utilizing a second mortality prediction model (e.g., the $MPM_0$ mortality prediction model), the second mortality prediction model being based on clinical data items collected within one hour of the patient being admitted to the Intensive Care Unit; determining a difference between the first mortality probability and the second mortality probability; and calculating the probability of mortality for the patient utilizing the following equation:

$$e^{Y_i}/(1+e^{Y_i}) \qquad \text{(Equation 1.)}$$

$Y_i$ is calculated utilizing the following equation:

$$Y_i = \beta_0 + (\beta_1)(A) + (\beta_2)(\lambda) + (\beta_3)(\delta_{(MA)}), \qquad \text{(Equation 2.)}$$

wherein $Y_i$ equals zero if the patient survives and one if the patient dies, wherein A equals the logit of the first mortality probability, wherein $\lambda$ equals the length of the first Intensive-Care-Unit-day under the APACHE® methodology, wherein $\delta_{(MA)}$ equals one if the difference between the second mortality probability and the first mortality probability exceeds 0.15 and zero if the difference between the second mortality probability and the first mortality probability is less than or equal to 0.15, and wherein the values for $\beta_0$, $\beta_1$, $\beta_2$, and $\beta_3$ are obtained through a logistic regression procedure using Equation 2.

In another embodiment, the present invention is directed to a method in a clinical computing environment for predicting a probability of mortality for a patient admitted to an Intensive Care Unit. The method includes determining a length of a first Intensive-Care-Unit-day for the patient (e.g., under the APACHE® methodology); calculating, via a first computing process, a first mortality probability utilizing the APACHE® mortality prediction model; calculating, via a second computing process, a second mortality probability utilizing the Mortality Probability Model at Admission (MPM$_0$) mortality prediction model; determining a difference between the second mortality probability and the first mortality probability; and calculating, via a third computing process, the probability of mortality for the patient utilizing Equation 1. $Y_i$ is calculated via a fourth computing process utilizing Equation 2, wherein $Y_i$ equals zero if the patient survives and one if the patient dies, wherein A equals the logit of the first mortality probability, wherein λ equals the length of the first Intensive-Care-Unit-day (e.g., under the APACHE® methodology), wherein $\delta_{(MA)}$ equals one if the difference between the second mortality probability and the first mortality probability exceeds 0.15 and zero if the difference between the second mortality probability and the first mortality probability is less than or equal to 0.15, and wherein values for $\beta_0$, $\beta_1$, $\beta_2$, and $\beta_3$ are obtained through a logistic regression procedure using Equation 2. The first, second, third, and fourth computing process are performed utilizing one or more computing devices.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The present invention is described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventor has contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

As previously set forth, embodiments of the present invention relate to methods in a clinical computing environment for predicting the probability of mortality in critically ill patients, that is, patients admitted to Intensive Care Units. (The terms "individual", "person", and "patient" are used interchangeably herein and are not meant to limit the nature of the referenced individual in any way. Further, use herein of the term "patient" is not meant to imply any particular relationship between the individual and those calculating predictive mortality probabilities.) In accordance with embodiments hereof, at least two distinctly different mortality prediction models are utilized in a multi-stage fashion to determine, with better accuracy than may be provided by either mortality prediction model alone, the probability of mortality for critically ill patients.

In accordance with embodiments hereof, four components are utilized to predict hospital mortality (defined as a patient death after admission to an ICU and before discharge from the hospital). The four components are: the length of the first Intensive-Care-Unit-day for the patient (e.g., under the APACHE® methodology), a first mortality probability calculated utilizing a mortality prediction model based on physiological data items collected within the patient's first Intensive-Care-Unit-day (e.g., the APACHE® mortality prediction model), a second mortality probability calculated utilizing a mortality prediction model based on clinical data items collected within one hour of the patient being admitted to the ICU (e.g., the MPM$_0$ mortality prediction model), and the difference between the probabilities generated by these two models. Each of these components is determined and inserted into a logistic regression model, as given in Equation 2:

$$Y_i = \beta_0(\beta_1)(A) + (\beta_2)(\lambda) + (\beta_3)(\delta_{(MA)}) \qquad \text{(Equation 2.)}$$

where $Y_i$ is equal to zero if the patient survives and one if patient does not survive;

A is equal to the logit of the APACHE® mortality probability;

λ is equal to the length of the first Intensive-Care-Unit-day (ranges from 0.333 to 1.333, as more fully described below); and $\delta_{(MA)}$ is equal to one if the difference between the second mortality probability and the first mortality probability is greater than 0.15 and zero if the difference between the second mortality probability and the first mortality probability is less than or equal to 0.15.

The values for $\beta_0$, $\beta_1$, $\beta_2$, and $\beta_3$ are obtained through a logistic regression procedure on a cohort of critically ill patients using the model in Equation 2. A patient's probability of mortality is then calculated utilizing Equation 1:

$$e^{Y_i}/(1+e^{Y_i}), \qquad \text{(Equation 1.)}$$

with $Y_i$ as given in Equation 2. Each of the variables in Equation 2, and their application thereto, is more fully described below.

Figure 1:
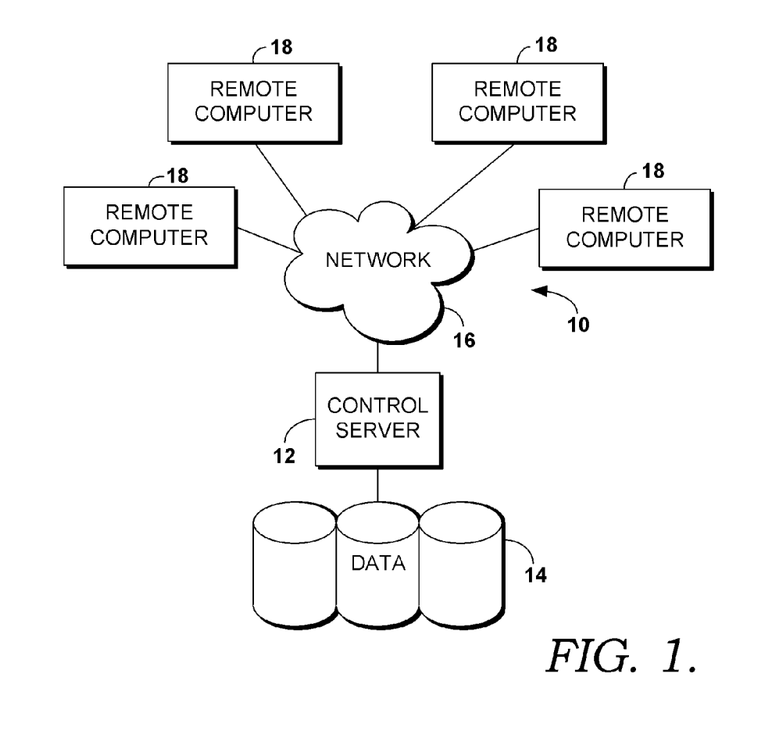
FIG. 1 is a block diagram of an exemplary computing environment suitable for use in implementing the present invention.

Referring to the drawings in general, and initially to FIG. 1 in particular, an exemplary computing system environment, for instance, a medical information computing system, on which embodiments of the present invention may be implemented is illustrated and designated generally as reference numeral 10. It will be understood and appreciated by those of ordinary skill in the art that the illustrated medical information computing system environment 10 is merely an example of one suitable computing environment and is not intended to suggest any limitation as to the scope of use or functionality of the invention. Neither should the medical information computing system environment 10 be interpreted as having any dependency or requirement relating to any single component or combination of components illustrated therein.

Embodiments of the present invention may be operational with numerous other general purpose or special purpose computing system environments or configurations. Examples of well-known computing systems, environments, and/or configurations that may be suitable for use with embodiments of the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 10 includes a general purpose computing device in the form of a control server 12. Components of the control server 12 may include, without limitation, a processing unit, internal system memory, and a suitable system bus for coupling various system components, including database cluster 14, with the server 12. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 12 typically includes, or has access to, a variety of computer readable media, for instance, database cluster 14. Computer readable media can be any available media that may be accessed by server 12, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 12. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 14, provide storage of computer readable instructions, data structures, program modules, and other data for the server 12.

The server 12 may operate in a computer network 16 using logical connections to one or more remote computers 18. Remote computers 18 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 18 may also be physically located in non-traditional medical care environments so that the entire health care community may be capable of integration on the network. The remote computers 18 may be personal computers, servers, routers, network PCs, peer devices, other common network nodes, or the like, and may include some or all of the components described above in relation to the server 12. The devices can be personal digital assistants or other like devices.

Exemplary computer networks 16 may include, without limitation, local area networks (LANs) and/or wide area networks (WANs). Such networking environments are commonplace in offices, enterprise-wide computer networks, intranets, and the Internet. When utilized in a WAN networking environment, the server 12 may include a modem or other means for establishing communications over the WAN, such as the Internet. In a networked environment, program modules or portions thereof may be stored in the server 12, in the database cluster 14, or on any of the remote computers 18. For example, and not by way of limitation, various application programs may reside on the memory associated with any one or more of the remote computers 18. It will be appreciated by those of ordinary skill in the art that the network connections shown are exemplary and other means of establishing a communications link between the computers (e.g., server 12 and remote computers 18) may be utilized.

In operation, a user may enter commands and information into the server 12 or convey the commands and information to the server 12 via one or more of the remote computers 18 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 12. In addition to a monitor, the server 12 and/or remote computers 18 may include other peripheral output devices, such as speakers and a printer.

Although many other internal components of the server 12 and the remote computers 18 are not shown, those of ordinary skill in the art will appreciate that such components and their interconnection are well known. Accordingly, additional details concerning the internal construction of the server 12 and the remote computers 18 are not further disclosed herein.

Although methods and systems of embodiments of the present invention are described as being implemented in a WINDOWS operating system, operating in conjunction with an Internet-based system, one of ordinary skill in the art will recognize that the described methods and systems can be implemented in any system supporting the receipt and processing of healthcare orders. As contemplated by the language above, the methods and systems of embodiments of the present invention may also be implemented on a stand-alone desktop, personal computer, or any other computing device used in a healthcare environment or any of a number of other locations.

As previously mentioned, embodiments of the present invention relate to a computerized method and system for use in, e.g., a healthcare computing environment, for predicting probabilities of mortality in critically ill patients, that is, patients admitted to Intensive Care Units (ICUs). In accordance with embodiments hereof, four components are utilized to predict hospital mortality (defined as a patient death after admission to an ICU and before discharge from the hospital). The four components are: the length of the first Intensive-Care-Unit-day for the patient (e.g., under the APACHE® methodology), a first mortality probability calculated utilizing a mortality prediction model based on physiological data items collected within the patient's first Intensive-Care-Unit-day (e.g., the APACHE® mortality prediction model), a second mortality probability calculated utilizing a mortality prediction model based on clinical data items collected within one hour of the patient being admitted to the ICU (e.g., the $MPM_0$ mortality prediction model), and the difference between the probabilities generated by these two models. Each of these components is determined and inserted into a logistic regression model, as given in Equation 2. A patient's probability of mortality is then calculated utilizing Equation 1. Each of these four components, and their use in predicting a patient's probability of mortality in accordance with embodiments of the present invention, is described more fully below.

The Length of the First Intensive-Care-Unit-Day for the Patient

The length of the first Intensive-Care-Unit-day is based upon when a patient is admitted to the ICU and which time that unit defines as the official start of the day. Most ICUs regard the official start of a day as 7:00 a.m. In accordance with embodiments hereof, the first Intensive-Care-Unit-day can range from 8 hours (0.333 days) to 32 hours (1.333 days). Thus, it is necessary for at least eight hours to elapse from the time of admission until the start of the next "day", or else the first day runs over into the actual second day the patient is in the ICU. Stated differently, a time the patient is admitted to the hospital is provided and it is then determined if a minimum of eight hours exists between the time that the patient is admitted to the ICU and the next subsequent ICU day's start (e.g., 7:00 a.m.). If a minimum of eight hours exists between the time that the patient is admitted to the ICU and the next subsequent day's start, the length of the first Intensive-Care-Unit-day is equal to the number of hours between the time the patient is admitted to the ICU and the next subsequent day's start. For example, assume that the ICU day "officially" begins at 7:00 a.m. on March $1^{st}$. A patient admitted at 8:30 a.m. would have a first Intensive-Care-Unit-day that ends at 7:00 a.m. the following day, March $2^{nd}$. Thus, the first Intensive-Care-Unit-day would be 22.5 hours in length. As another example, for a patient admitted at 10:00 p.m. on March $1^{st}$, the next official day would begin at 7:00 a.m. on March $2^{nd}$. As this is nine hours away, which is greater than eight hours, the patient's first Intensive-Care-Unit-day would be nine hours long.

However, if a minimum of eight hours does not exist between the time that the patient is admitted to the ICU and the next subsequent day's start, the length of the first Intensive-Care-Unit-day for the patient is equal to the number of hours between the time the patient is admitted to the ICU and the next subsequent day's start plus twenty-four. Thus, assuming again that the ICU day "officially" begins at 7:00 a.m. on March $1^{st}$, for a patient admitted at 4:00 a.m. on March $1^{st}$, the next official day would begin at 7:00 a.m., which would only be three hours away. Since this is less than eight hours, the first Intensive-Care-Unit-day would not end until 7:00 a.m. March $2^{nd}$. Thus, the first Intensive-Care-Unit-day would be three hours plus twenty-four hours, or 27 hours in length.

The First Mortality Probability

The first mortality probability is calculated utilizing a mortality prediction model based on physiological data items collected within the patient's first Intensive-Care-Unit-day (as defined herein above). One such mortality prediction model is the APACHE® mortality prediction model. By way of example, the APACHE® predictive model utilized herein is APACHE® IV's Equation 90, which yields a prediction on ICU day one that a patient will expire prior to discharge from the hospital. It is well described in Zimmerman J. E., Kramer A. A., McNair, D. S., Malila, F.: *Acute Physiology and Chronic Health Evaluation (APACHE) IV: Hospital Mortality Assessment for Today's Critical Ill Patients*, Critical Care Medicine, vol. 34, No. 5, pp. 1297-1310 (2006), which is incorporated herein by reference in its entirety. The formula is shown below:

$$\text{Prediction} = e^{(tempvar)}/(1 + e^{(tempvar)}) \quad \text{(Equation 3.)}$$

Tempvar is the sum of the coefficients (described below) multiplied by the value of each variable. Thus, tempvar=−5.95047195+

+0.24907346*patient had emergency surgery (Yes=1; No=0);

+0.78576432*patient sedated and couldn't have Glasgow Coma Score taken (Yes=1; No=0);

+0.27176004*patient was ventilated anytime during the first Intensive-Care-Unit-day (Yes=1; No=0);

−0.57987404*patient had acute myocardial infarction and received thrombolytic therapy (Yes=1; No=0);

+0.03911753*(15−Glasgow Coma Score);

+0.95810052*patient has AIDS (Yes=1; No=0);

+0.81466509*patient has Cirrhosis (Yes=1; No=0);

+1.03737993*patient has hepatic failure (Yes=1; No=0);

+0.43558108*patient has a suppressed immune system (Yes=1; No=0);

+0.74347175*patient has a lymphoma (Yes=1; No=0);

+0.96930830*patient had a myeloma (Yes=1; No=0);

+1.08642375*patient has a tumor with metastases (Yes=1; No=0);

+0.01714919*patient was admitted to the ICU from the general floor (Yes=1; No=0);

+0.02210627*patient was admitted to the ICU from another hospital (Yes=1; No=0);

−0.58382812*patient was admitted to the ICU from the operating room (Yes=1; No=0);

−0.000.9707*($P_aO_2$:$F_iO_2$ ratio);

+0.05563492*Acute Physiology Score;

+8.7185221E-6*(maximum of (acute physiology score−10, 0)**3);

−0.00004511*(maximum of (acute physiology score−22, 0)**3);

+0.00005038*(maximum of (acute physiology score−32, 0)**3);

−0.000013123*(maximum of (acute physiology score−48, 0)**3);

−8.653492E-7*(maximum of (acute physiology score−89, 0)**3);

+0.02417746*the patient's age;
−4.388616E-6*(maximum of (the patient's age−27, 0)**3);
+0.0000501422*(maximum of (the patient's age−51, 0)**3);
−0.000127787*(maximum of (the patient's age−64, 0)**3);
+0.000109606*(maximum of (the patient's age−74, 0)**3);
−0.000027572*(maximum of (the patient's age−86, 0)**3);
−0.31048750*PRELOS2;
+1.4746725115*(maximum of (PRELOS2−0.121, 0)**3);
−2.8618857*(maximum of (PRELOS2−0.423, 0)**3);
+1.4216590103*(maximum of (PRELOS2−2.806, 0)**3); and
+coefficient for the specific diagnostic group, wherein PRELOS2=the square root of (ICU admission date time−hospital admission date time), and the specific diagnostic groups and their coefficients can be found in Appendix Table I & Appendix Table 2 of Zimmerman J. E., Kramer A. A., McNair, D. S., Malila, F.: *Acute Physiology and Chronic Health Evaluation (APACHE) IV. Hospital Mortality Assessment for Today's Critical Ill Patients*, Critical Care Medicine, vol. 34, No. 5, pp. 1297-1310 (2006).

It should be noted that the model version utilized herein is by way of example only and that as newer versions of the APACHE® mortality prediction model are developed, the same may be utilized to replace the model described herein above within embodiments of the present invention.

The Second Mortality Probability

The second mortality probability is calculated utilizing a mortality prediction model based on clinical data items collected within one hour of the patient being admitted to the ICU. One such mortality prediction model is the $MPM_0$ mortality prediction model. By way of example, the version utilized herein is $MPM_0$-III, which yields a prediction on ICU day 1 that a patient will expire prior to discharge from the hospital. It is well described in Higgins, T. L., Teres, D., Copes, W. S., Nathanson, B. H., Stark, M., Kramer, A. A., *Assessing Contemporary Intensive Care Unit Outcome: An Updated Mortality Probability Admission Model ($MPM_0$-III)*, Critical Care Medicine, vol. 35, No. 3, pp. 827-835 (2007), which is incorporated herein by reference in its entirety. The equation's formula is the same as Equation 3. However, tempvar is calculated based upon different criteria and coefficients. In the $MPM_0$-III mortality prediction model, tempvar is calculated as −5.36282943

+2.05051409*Glasgow Coma Score of {3, 4, or 5} (Yes=1; No=0);
+0.43318797*heart rate≧150 (Yes=1; No=0);
+1.45100535*systolic blood pressure≦90 (Yes=1; No=0);
+0.53952084*patient has chronic renal failure (Yes=1; No=0);
+2.07069492*patient has cirrhosis (Yes=1; No=0);
+3.20490153*patient has stage IV cancer (Yes=1; No=0);
+0.84122738*patient has acute renal failure (Yes=1; No=0);
+0.82196119*patient has a cardiac dysrhythmia (Yes=1; No=0);
+0.41076857*patient experienced a cerebrovascular incident (Yes=1; No=0);
−0.16525304*patient has gastrointestinal bleeding (Yes=1; No=0);
+1.85527584*patient has an intracranial mass (Yes=1; No=0);
+1.49725829*patient had cardiopulmonary resuscitation within 24 hours of ICU admission (Yes=1; No=0);
+0.82164799*patient is on a ventilator within one hour of ICU admission (Yes=1; No=0);
+0.90979355*patient is a medical or unscheduled surgical admission (Yes=1; No=0);
+0.03855816*the patient's age;
−0.79697823*patient had no restrictions on therapies or interventions (Yes=1; No=0);
−0.42435249*patient is an elective surgery admission and has no other MPM risk factors, excluding {no restrictions on therapies or interventions} (Yes=1; No=0);
−0.00851969*age*systolic blood pressure<90 (Yes=1; No=0);
−0.02243335*the patient's age*patient has cirrhosis (Yes=1; No=0);
−0.03302375*the patient's age*patient has stage IV cancer (Yes=1; No=0);
−0.01012856*the patient's age*patient has a cardiac dysrhythmia (Yes=1; No=0);
−1.10692152*the patient's age*patient has an intracranial mass (Yes=1; No=0);
−0.01121395*the patient's age*patient had cardiopulmonary resuscitation within 24 hours of ICU admission (Yes=1; No=0); and
−0.00752843*the patient's age*Glasgow Coma Score of {3, 4, or 5} (Yes=1; No=0).

The specific definitions for the terms in the $MPM_0$-III model can be found in Appendix B of Higgins, T. L., Teres, D., Copes, W. S., Nathanson, B. H., Stark, M., Kramer, A. A., *Assessing Contemporary Intensive Care Unit Outcome: An Updated Mortality Probability Admission Model ($MPM_0$-III)*, Critical Care Medicine, vol. 35, No. 3, pp. 827-835 (2007).

It should be noted that the model version utilized herein is by way of example only and that as newer versions of the $MPM_0$ mortality prediction model are developed, the same may be utilized to replace the model described herein above within embodiments of the present invention.

Difference Between the Second Mortality Probability and the First Mortality Probability This is a binary variable based on whether a patient's second (e.g., $MPM_0$-III) mortality probability is substantially greater than their first (e.g., APACHE®) mortality probability. The reasoning is that if a patient's condition at admission improves substantially during the day, then this will manifest itself as the second mortality prediction (that is, the mortality prediction based upon clinical data items collected within one hour of the patient being admitted to the ICU) being much higher than the first mortality prediction (that is, the mortality prediction based on physiological data items collected within the patient's first Intensive-Care-Unit-day under the APACHE® methodology). The variable is set equal to one if a patient's second mortality probability is larger than their first mortality probability by more than 0.15. If not, then the variable is set to zero.

A Multi-Stage Approach to Predicting Probabilities of Mortality

Figure 2:
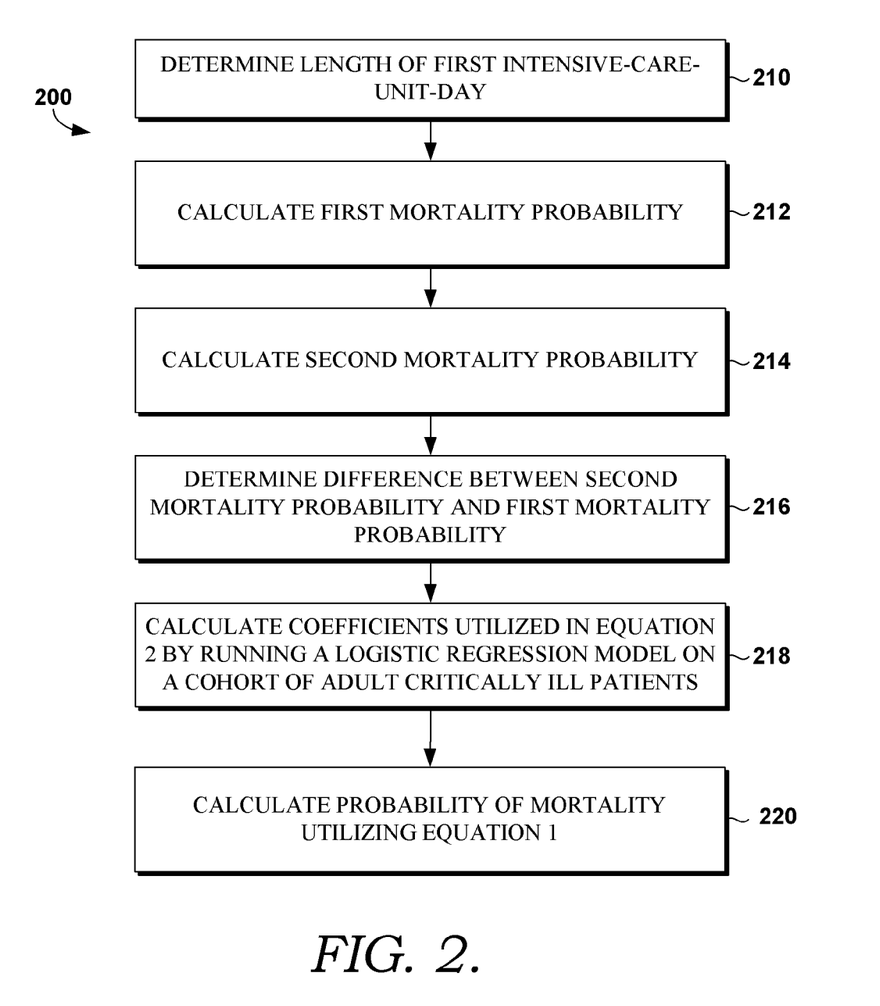
FIG. 2 is a flow diagram showing a method for predicting a probability of mortality for a patient admitted to an Intensive Care Unit, in accordance with an embodiment of the present invention.

With reference now to FIG. 2, a flow chart representative of a method for predicting probabilities of mortality for critically ill patients, in accordance with an embodiment of the present invention, is illustrated and depicted generally as reference numeral 200. Method 200 may be implemented on the above-described exemplary computing system environment (FIG. 1) and, by way of example only, may be utilized to predict mortality probabilities for patients admitted to Intensive Care Units.

As shown at block 210, the length of a first Intensive-Care-Unit-day for the patient is determined. The length may be calculated as described herein above and may range from 0.333 days to 1.333 days. As indicated at block 212, a first mortality probability is calculated utilizing a first mortality prediction model, the first mortality prediction model being based on physiological data items collected within the patient's first Intensive-Care-Unit-day. In one embodiment, the first mortality probability is calculated utilizing the APACHE® mortality prediction model, as described herein above.

As indicated at block 214, a second mortality probability is calculated utilizing a second mortality prediction model, the second mortality prediction model being based on clinical data items collected within one hour of the patient being admitted to the Intensive Care Unit. In one embodiment, the second mortality probability is calculated utilizing the $MPM_0$ mortality prediction model, as described herein above.

As shown at block 216, the difference between the second mortality probability and the first mortality probability is determined. As shown at block 218, the variables in blocks 210, 212, 214 and 216 are included in a logistic regression equation to derive the coefficients in Equation 2. Then, as indicated at block 220, the probability of mortality for the patient is calculated. The probability of mortality of the patient is calculated utilizing the following equation:

$$e^{Y_i}/(1+e^{Y_i}) \quad \text{(Equation 1.)}$$

$Y_i$ is calculated utilizing the following equation:

$$Y_i = \beta_0 + (\beta_1)(A) + (\beta_2)(\lambda) + (\beta_3)(\delta_{(MA)}), \quad \text{(Equation 2.)}$$

wherein $Y_i$ equals zero if the patient survives and one if the patient dies, A equals the logit of the first mortality probability, $\lambda$ equals the length of the first Intensive-Care-Unit-day, wherein $\delta_{(MA)}$ equals one if the difference between the second mortality probability and the first mortality probability exceeds 0.15 and zero if the difference between the second mortality probability and the first mortality probability is less than or equal to 0.15, and the values for $\beta_0$, $\beta_1$, $\beta_2$, and $\beta_3$ are obtained through a logistic regression procedure using Equation 2.

Use Case Example

A sample of 4,072 patients admitted to twenty ICUs in the U.S. were studied. Information was obtained on all variables necessary to generate a mortality probability based on the APACHE® mortality prediction model, as well as a mortality probability based on the $MPM_0$ mortality prediction model. Each patient had those predictions calculated, along with the duration of their first Intensive-Care-Unit-day. These data items were fed into the logistic regression equation of Equation 2 (above) to solve for $\beta_0$, $\beta_1$, $\beta_2$, and $\beta_3$. Table 1 shows the results of the logistic regression procedure.

TABLE 1

| Variable | Value | p-value | Odds Ratio |
|---|---|---|---|
| Intercept ($\beta_0$) | 0.1002 | N/A | N/A |
| APACHE ® Logit ($\beta_1$) | 1.0047 | <0.0001 | 2.731 |
| Length of APACHE ® Day 1 ($\beta_2$) | −0.4378 | 0.0133 | 0.645 |
| (MPM − APACHE ®) > 0.15? ($\beta_3$) | 0.6435 | <0.0001 | 1.903 |

All of the coefficients are statistically significant. The odds ratio for the APACHE® probability's logit is 2.73, indicating that the APACHE® prediction is very important. The duration of the first Intensive-Care-Unit-day had a negative coefficient, so the odds ratio was <1.00. In essence, that odds ratio indicates that going from 8 hours to 32 hours results in a relative decrease in predicted mortality of 35.5%. This has clinical validity, as the longer the duration of the first Intensive-Care-Unit-day, the longer that intervening therapies have an opportunity to be effective. Finally, the coefficient for an $MPM_0$ prediction being more than 15% greater than an APACHE® prediction resulted in almost a doubling of risk. This indicates that when the $MPM_0$ probability is much higher than the APACHE® probability, the latter is not imparting sufficient information, or response to therapy has been minimal.

Evaluation of the Multi-Stage Mortality Prediction Model

To identify whether the multi-stage mortality prediction model yields better mortality predictions than prior existing models generate individually, it was necessary to calculate relevant statistics of accuracy. Measures of assessing a model's predictive capability fall into two types: discrimination and calibration. Discrimination is the ability of a model to distinguish between a pair of observations with discordant outcomes. That is, it is the percentage of times that an observation with an outcome equal to "1" will have a higher probability than an observation with an outcome equal to "0." The commonly accepted measure of discrimination is the area under the Receiver Operating Characteristics curve (AU-ROC), as will be understood by those of ordinary skill in the art.

Calibration, on the other hand, looks at the concordance of observed and predicted values across the probability range. The most frequently used measure is the Hosmer-Lemeshow Goodness-of-Fit statistic (H-L Statistic). However, it has been demonstrated that this statistic is overly sensitive to the large populations utilized in critical care studies. Thus, it has to be supplemented by other measures, most notably, the standardized mortality ratio (SMR), calibration graph (mean observed mortality vs. mean predicted mortality over deciles of predicted risk), coefficient of determination, Brier Score, Shapiro's R, and Cox's calibration regression. It should be noted that for SMR, values close to 1.00 are good. Smaller values are better for the H-L Statistic and the Brier Score. Larger values are better for the AU-ROC, coefficient of determination, Shapiro's R, and the $R^2$ from the Cox's calibration regression.

For the use case described above, each of these measures was calculated under three scenarios: using the APACHE® IV model only to predict mortality, using the $MPM_0$-III model only to predict mortality, and using the multi-stage model described herein to predict mortality. The results are shown in Table 2.

TABLE 2

| Model | APACHE ® | $MPM_0$-III | Multi-Stage |
|---|---|---|---|
| SMR (95% C.I.) | 0.997 | 0.999 | 0.997 |
|  | (0.930, 1.064) | (0.926, 1.073) | (0.931, 1.064) |
| AU-ROC | 0.873 | 0.787 | 0.877 |
| H-L Statistic | 9.752 | 7.294 | 8.172 |
| Coeff. of Determination | 0.402 | 0.232 | 0.411 |
| Brier Score | 0.078 | 0.090 | 0.077 |
| Shapiro's R | 0.271 | 0.196 | 0.277 |
| Cox Calibration regression ($R^2$) | 0.298 | 0.156 | 0.305 |

The multi-stage model had the highest discrimination, coefficient of determination, Shapiro's R, and $R^2$ from Cox's calibration regression. It also had the lowest Brier Score. The $MPM_0$-III model had the lowest H-L Statistic. All three models have nearly identical SMRs. These results indicate that the multi-stage model is capable of producing better results than either the APACHE® IV-only model or the $MPM_0$-III-only model.

As can be understood, embodiments of the present invention provide computerized methods and systems for use in, e.g., a healthcare computing environment, for predicting the probability of mortality in critically ill patients, that is, patients admitted to Intensive Care Units. In accordance with embodiments hereof, at least two distinctly different mortality prediction models are utilized in a multi-stage fashion to determine, with better accuracy than may be provided by either mortality prediction model alone, the probability of mortality for critically ill patients.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and sub-combinations are of utility and may be employed without reference to other features and sub-combinations. This is contemplated by and within the scope of the claims.

What is claimed is:

1. One or more non-transitory computer-storage media having computer-executable instructions embodied thereon for performing a method in a clinical computing environment for predicting a probability of mortality for a patient admitted to an Intensive Care Unit, the method comprising:
    determining a length of a first Intensive-Care-Unit-day for the patient;
    calculating a first mortality probability utilizing a first mortality prediction model, the first mortality prediction model being based on physiological data items collected within the patient's first Intensive-Care-Unit-day;
    calculating a second mortality probability utilizing a second mortality prediction model, the second mortality prediction model being based on clinical data items collected within one hour of the patient being admitted to the Intensive Care Unit;
    determining a difference between the second mortality probability and the first mortality probability;
    calculating the probability of mortality for the patient utilizing Equation 1:

$$e^{Y_i}/(1+e^{Y_i}),$$

wherein $Y_i$ is calculated utilizing Equation 2:

$$Y_i = \beta_0 + (\beta_1)(A) + (\beta_2)(\lambda) + (\beta_3)(\delta_{(MA)}),$$

wherein $Y_i$ equals zero if the patient survives and one if the patient dies, wherein A equals the logit of the first mortality probability, wherein $\lambda$ equals the length of the first Intensive-Care-Unit-day, wherein $\delta_{(MA)}$ equals one if the difference between the second mortality probability and the first mortality probability exceeds 0.15 and zero if the difference between the second mortality probability and the first mortality probability is less than or equal to 0.15, and wherein values for $\beta_0$, $\beta_1$, $\beta_2$, and $\beta_3$ are obtained through a logistic regression procedure using Equation 2; and
    assessing ICU performance by comparing observed and predicted mortality.

2. The one or more computer-storage media of claim 1, wherein determining the length of the first Intensive-Care-Unit-day for the patient comprises:
    providing a time that the patient is admitted to the Intensive Care Unit;
    determining if a minimum of eight hours exists between the time that the patient is admitted to the Intensive Care Unit and the next subsequent day's start time,
    wherein if a minimum of eight hours exists between the time that the patient is admitted to the Intensive Care Unit and the next subsequent day's start time, the length of the first Intensive-Care-Unit day for the patient is equal to the number of hours between the time that the patient is admitted to the Intensive Care Unit and the next subsequent day's start time,
    and wherein if a minimum of eight hours does not exist between the time that the patient is admitted to the Intensive Care Unit and the next subsequent day's start time, the length of the first Intensive-Care-Unit day for the patient is equal to the number of hours between the time that the patient is admitted to the Intensive Care Unit and the next subsequent day's start time plus twenty-four.

3. The one or more computer-storage media of claim 1, wherein calculating the first mortality probability utilizing the first mortality prediction model comprises calculating the first mortality probability utilizing the Acute Physiology and Chronic Health Evaluation mortality prediction model.

4. The one or more computer-storage media of claim 3, wherein calculating the first mortality probability utilizing the Acute Physiology and Chronic Health Evaluation mortality prediction model comprises calculating the first mortality probability utilizing the Acute Physiology and Chronic Health Evaluation IV mortality prediction model.

5. The one or more computer-storage media of claim 1, wherein calculating the second mortality probability utilizing the second mortality prediction model comprises calculating the second mortality probability utilizing the Mortality Probability Model at Admission.

6. The one or more computer-storage media of claim 5, wherein calculating the second mortality probability utilizing the Mortality Probability Model at Admission comprises calculating the second mortality probability utilizing the Mortality Probability Model at Admission, version III.

7. The one or more computer-storage media of claim 1,
    wherein calculating the first mortality probability utilizing the first mortality prediction model comprises calculating the first mortality probability utilizing the Acute Physiology and Chronic Health Evaluation mortality prediction model,
    and wherein calculating the second mortality probability utilizing the second mortality prediction model comprises calculating the second mortality probability utilizing the Mortality Probability Model at Admission.

8. The one or more computer-storage media of claim 7,
    wherein calculating the first mortality probability utilizing the Acute Physiology and Chronic Health Evaluation mortality prediction model comprises calculating the first mortality probability utilizing the Acute Physiology and Chronic Health Evaluation IV mortality prediction model,
    and wherein calculating the second mortality probability utilizing the Mortality Probability Model at Admission comprises calculating the second mortality probability utilizing the Mortality Probability Model at Admission, version III.

9. A method in a clinical computing environment for predicting a probability of mortality for a patient admitted to an Intensive Care Unit, the method comprising:
   determining a length of a first Intensive-Care-Unit-day for the patient;
   calculating, via a first computing process, a first mortality probability utilizing the Acute Physiology and Chronic Health Evaluation mortality prediction model;
   calculating, via a second computing process, a second mortality probability utilizing the Mortality Probability Model at Admission mortality prediction model;
   determining a difference between the second mortality probability and the first mortality probability;
   calculating, via a third computing process, the probability of mortality for the patient utilizing Equation 1:

$$e^{Y_i}/(1+e^{Y_i}),$$

wherein $Y_i$ is calculated via a fourth computing process utilizing Equation 2:

$$Y_i = \beta_0 + (\beta_1)(A) + (\beta_2)(\lambda) + (\beta_3)(\delta_{(MA)}),$$

wherein $Y_i$ equals zero if the patient survives and one if the patient dies, wherein A equals the logit of the first mortality probability, wherein $\lambda$ equals the length of the first Intensive-Care-Unit-day, wherein $\delta_{(MA)}$ equals one if the difference between the second mortality probability and the first mortality probability exceeds 0.15 and zero if the difference between the second mortality probability and the first mortality probability is less than or equal to 0.15, and wherein values for $\beta_0$, $\beta_1$, $\beta_2$, and $\beta_3$ are obtained through a logistic regression procedure using Equation 2,
   and wherein the first, second, third, and fourth computing process are performed utilizing one or more computing devices; and
   assessing ICU performance by comparing observed and predicted mortality.

10. The method of claim 9, wherein determining the length of the first Intensive-Care-Unit-day for the patient comprises:
   providing a time that the patient is admitted to the Intensive Care Unit;
   determining if a minimum of eight hours exists between the time that the patient is admitted to the Intensive Care Unit and the next subsequent day's start time,
   wherein if a minimum of eight hours exists between the time that the patient is admitted to the Intensive Care Unit and the next subsequent day's start time, the length of the first Intensive-Care-Unit day for the patient is equal to the number of hours between the time that the patient is admitted to the Intensive Care Unit and the next subsequent day's start time,
   and wherein if a minimum of eight hours does not exist between the time that the patient is admitted to the Intensive Care Unit and the next subsequent day's start time, the length of the first Intensive-Care-Unit day for the patient is equal to the number of hours between the time that the patient is admitted to the Intensive Care Unit and the next subsequent day's start time plus twenty-four.

11. The method of claim 9, wherein calculating, via the first computing process, the first mortality probability utilizing the Acute Physiology and Chronic Health Evaluation mortality prediction model comprises calculating the first mortality probability utilizing the Acute Physiology and Chronic Health Evaluation IV mortality prediction model.

12. The method of claim 9, wherein calculating, via the second computing process, the second mortality probability utilizing the Mortality Probability Model at Admission mortality prediction model comprises calculating the second mortality probability utilizing the Mortality Probability Model at Admission, version III.

13. The method of claim 9,
   wherein calculating, via the first computing process, the first mortality probability utilizing the Acute Physiology and Chronic Health Evaluation mortality prediction model comprises calculating the first mortality probability utilizing the Acute Physiology and Chronic Health Evaluation IV mortality prediction model,
   and wherein calculating, via the second computing process, the second mortality probability utilizing the Mortality Probability Model at Admission mortality prediction model comprises calculating the second mortality probability utilizing the Mortality Probability Model at Admission, version III.

\* \* \* \* \*